United States Patent [19]

Navab et al.

[11] Patent Number: 5,822,396
[45] Date of Patent: Oct. 13, 1998

[54] CALIBRATION SYSTEM AND METHOD FOR X-RAY GEOMETRY

[75] Inventors: Nassir Navab, Plainsboro; Ali Reza Bani-Hashemi, Belle Mead, both of N.J.

[73] Assignee: Siemens Corporate Research, Inc., Princeton, N.J.

[21] Appl. No.: 893,283

[22] Filed: Jul. 15, 1997

Related U.S. Application Data

[63] Continuation of Ser. No. 576,718, Dec. 21, 1995, abandoned.

[51] Int. Cl.⁶ .................................................. G01D 18/00
[52] U.S. Cl. ............................................ 378/207; 378/163
[58] Field of Search .................................. 378/162, 163, 378/164, 207

[56] References Cited

U.S. PATENT DOCUMENTS

| | | | |
|---|---|---|---|
| 3,952,194 | 4/1976 | Bayonnet | 250/358 |
| 4,319,136 | 3/1982 | Jinkins | 378/4 |
| 4,341,220 | 7/1982 | Perry | 128/630 |
| 4,400,819 | 8/1983 | Bens et al. | 378/20 |
| 4,838,265 | 6/1989 | Cosman et al. | 606/1 |
| 4,884,566 | 12/1989 | Mountz et al. | 128/303 |
| 4,915,112 | 4/1990 | Singer | 128/653 |
| 4,971,060 | 11/1990 | Schneider et al. | 128/653.1 |
| 5,216,700 | 6/1993 | Cherian | 378/163 |
| 5,260,985 | 11/1993 | Mosby | 378/164 |

FOREIGN PATENT DOCUMENTS

| | | |
|---|---|---|
| 377 689 | 6/1980 | Austria . |
| 0 018 166 A1 | 10/1980 | European Pat. Off. . |
| 2 700 909-A1 | 7/1994 | France . |
| 27 35 250 A1 | 2/1979 | Germany . |
| 40 29 590 A1 | 7/1991 | Germany . |
| WO X94/02477 | 5/1995 | WIPO . |

OTHER PUBLICATIONS

International Search Report dated Jun. 13, 1997.

*Primary Examiner*—David P. Porta
*Assistant Examiner*—David Vernon Bruce
*Attorney, Agent, or Firm*—Adel A. Ahmed

[57] ABSTRACT

A system for X-ray geometry calibration comprises a calibration frame adapted for mounting proximate to at least a portion of a patient's body, such as a patient's head. An X-ray source cooperates with a target at a given orientation and distance from the portion of a patient's body for forming an image of the portion of a patient's body and of at least an associated portion of the calibration frame. The calibration frame includes encoding arrangement for uniquely determining correspondence between the image of the associated portion of the calibration frame and the calibration frame such that the orientation and distance can be determined uniquely from the image of the associated portion of the calibration frame.

33 Claims, 8 Drawing Sheets

CALIBRATION SYSTEM AND METHOD FOR X-RAY GEOMETRY

CROSS-REFERENCE TO RELATED APPLICATION

This is a continuation of Ser. No. 08/576,718 filed Dec. 21, 1995 now abandoned.

The present application relates to a system and method for calibrating the geometry in an X-ray imaging configuration, and more particularly to a system wherein correlation can be established between a three dimensional object and a two-dimensional image.

There has been increasing interest in the reconstruction of vessel trees from X-ray angiograms, for which there are many applications. Various methods have been proposed and some such methods attempt to take into account the dynamics of the contrast bolus as it evolves over the Digital Subtraction Angiograph (DSA) sequence. These methods usually assume that the imaging system, that is the X-ray source and image intensifier system are rotating around a patient and are well calibrated. They therefore use the geometry of the imaging system for reconstruction of the vessel tree.

However, in practice many X-ray systems are not well calibrated, and the errors in calibration propagate through the reconstruction process and reduce the accuracy of the results.

Reference is hereby also made to a copending application in the name of the present inventors entitled CALIBRATION APPARATUS FOR X-RAY GEOMETRY and filed on even date with the present application. The said copending application is directed to closely related subject matter to the present application and the disclosure thereof, to the extent it is not inconsistent with the present application, is incorporated herein by reference.

Briefly, the said copending application discloses calibration apparatus for X-ray geometry, for use in conjunction with a portion of a patient's body to be X-rayed, an X-ray source, and imaging arrangement for forming an image, wherein the imaging arrangement is at a given orientation and distance from the portion of a patient's body, comprises a calibration ring adapted for being fastened to a portion of a patient's body, the ring exhibiting a first degree of transparency to X-rays; and an encoding arrangement incorporated in the ring, comprising a plurality of encoding units exhibiting a second degree of transparency to X-rays, different from the first degree, the encoding units being arranged in a predetermined configuration such that an essentially two-dimensional projected image, formed by the imaging arrangement, of the calibration ring with the encoding arrangement exhibits a pattern of contrasting intensity attributable to at least a portion of the encoding arrangement from which the orientation and distance can be determined uniquely.

The said copending application further discloses calibration apparatus for use in conjunction with X-ray imaging for establishing correspondence between a three-dimensional object and its two dimensional projection image, comprises a calibration ring associated with a portion of the anatomy of a subject for X-ray examination, the ring comprising: a carrier portion adapted for attachment to the subject; encoding arrangement incorporated in the carrier portion of the calibration ring, the encoding arrangement comprising a plurality of code word configurations formed of a substance having a different degree of transparency from that of the carrier portion, the code word configurations being arranged in a sequence separated by spaces along a circumferential path along the ring in a given sense in which such words are to be read, such that no code word occurs more than once and no code word forms a valid word when read in a sense opposite the given sense.

The said copending application also discloses calibration apparatus for use in conjunction with X-ray imaging for establishing correspondence between a three-dimensional object and its two dimensional projection image, comprises a calibration ring associated with a portion of the anatomy of a subject for X-ray examination, the ring comprising: a carrier portion adapted for attachment to the subject; encoding arrangement incorporated in the carrier portion of the calibration ring, the encoding arrangement comprising a plurality of code word configurations formed of a substance for casting a calibration image in contrast to that of the carrier portion, such that the correspondence can be established uniquely from a portion, less than the whole, of the calibration image.

It is herein recognized that the algorithm in accordance with the present invention should provide for dynamic calibration of an X-ray system by introducing landmarks positioned around the patient within the region of interest. One object of the present invention is to achieve an intelligent design of such landmarks to obtain the most efficient and reliable calibration procedure.

In accordance with an aspect of the invention, a calibration frame comprises a set of ball bearings positioned on a cylinder, herein referred to as a calibration ring. The structure of the calibration ring has been simulated. Different views of the calibration ring and, in particular, its image within a typical X-ray imaging system, are illustrated by using a simulation procedure in Maple.

In accordance with an aspect of the invention, system for X-ray geometry calibration comprises a calibration frame adapted for mounting proximate to at least a portion of a patient's body; an X-ray source; a target at a given orientation and distance from the portion of a patient's body for cooperating with the X-ray source for forming an image of the portion of a patient's body and of at least an associated portion of the calibration frame; and wherein the calibration frame includes encoding arrangement for uniquely determining correspondence between the image of the associated portion of the calibration frame and the calibration frame such that the orientation and distance can be determined uniquely from the image of the associated portion of the calibration frame.

In accordance with another aspect of the invention, the image of the portion of a patient's body and of the associated portion of the calibration frame is contained in a substantially flat plane.

In accordance with still another aspect of the invention, the encoding arrangement comprises at least a portion of the calibration frame exhibiting first portions thereof that are relatively opaque to X-rays and second portions that are relatively transparent to X-rays.

In accordance with yet another aspect of the invention, the encoding arrangement comprises an encoded arrangement of the first portions.

In accordance with still another aspect of the invention, the encoding arrangement comprises an encoded arrangement of the second portions.

In accordance with a further aspect of the invention, the encoding arrangement comprises an encoded arrangement of the first and second portions.

In accordance with still a further aspect of the invention, the first portions of the calibration frame are formed by metallic spherules.

In accordance with yet a further aspect of the invention, the second portions of the calibration frame are formed by holes in the calibration frame.

In accordance with a further aspect of the invention, the calibration frame exhibits a three-dimensional form.

In accordance with another aspect of the invention, the calibration frame exhibits characteristics such that it can be determined from the image in the substantially flat plane which portions of the three-dimensional form are proximate the image in the substantially flat plane and which portions are distal therefrom.

In accordance with still another aspect of the invention, the calibration frame exhibits a three-dimensional form.

In accordance with yet another aspect of the invention, the calibration frame comprises a flat ribbon-like structure.

In accordance with a further aspect of the invention, the flat ribbon-like structure is formed into an endless loop.

In accordance with yet a further aspect of the invention, the image of the portion of a patient's body and of the associated portion of the calibration frame is contained in a two-dimensional surface.

In accordance with an aspect of the invention, the calibration frame is adapted for fastening to a patient's head.

In accordance with an aspect of the invention, a system for X-ray geometry calibration comprises a calibration frame associated with a portion of a patient's body; an X-ray source; arrangement for forming an X-ray image of the portion of a patient's body and of the associated portion of the calibration frame; and wherein the calibration frame comprises encoding arrangement for determining a correspondence between the image of the associated portion of the calibration frame and the calibration frame for uniquely determining the correspondence uniquely from the image of the associated portion of the calibration frame.

In accordance with another aspect of the invention, method for determining correspondence between an X-ray image of a calibration frame associated with at least a portion of the body of a patient and the position of the calibration frame with respect to X-ray apparatus, comprises the steps of: (a) positioning an encoded three-dimensional calibration frame relative to at least a portion of a patient's body; (b) exposing the portion of a patient's body and at least a portion of the calibration frame to an X-ray source at a given orientation and distance therefrom so as to form a projected image of the portion of a patient's body and of the portion of the calibration frame; and (c) uniquely determining a correspondence between the image of the portion of the calibration frame and the three-dimensional calibration frame from observations of the image such that the orientation and distance are uniquely determined.

In accordance with yet another aspect of the invention, a method for determining correspondence between an X-ray image of a calibration frame associated with at least a portion of the body of a patient and the position of the calibration frame with respect to X-ray apparatus, comprises the steps of: (a) positioning an encoded three-dimensional calibration frame relative to at least a portion of a patient's body, the calibration frame including therein an arrangement of spherules; (b) exposing the portion of a patient's body and at least a portion of the calibration frame to an X-ray source at a given orientation and distance therefrom so as to form a projected image of the portion of a patient's body and of the portion of the calibration frame; and (c) uniquely determining a correspondence between the image of the portion of the calibration frame and the three-dimensional calibration frame from observations of the image; and (d) computing the orientation and distance.

The invention will be more fully understood from the following detailed description, in conjunction with the drawing, in which.

Figure 5:
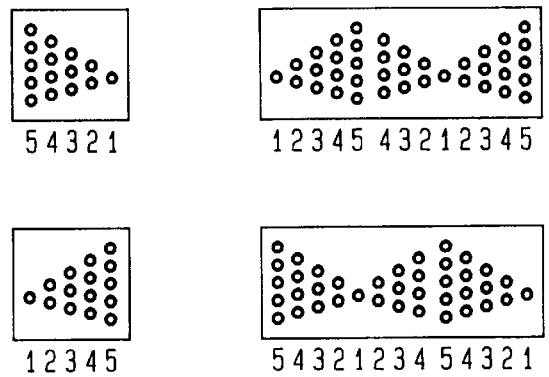
Figure 6:
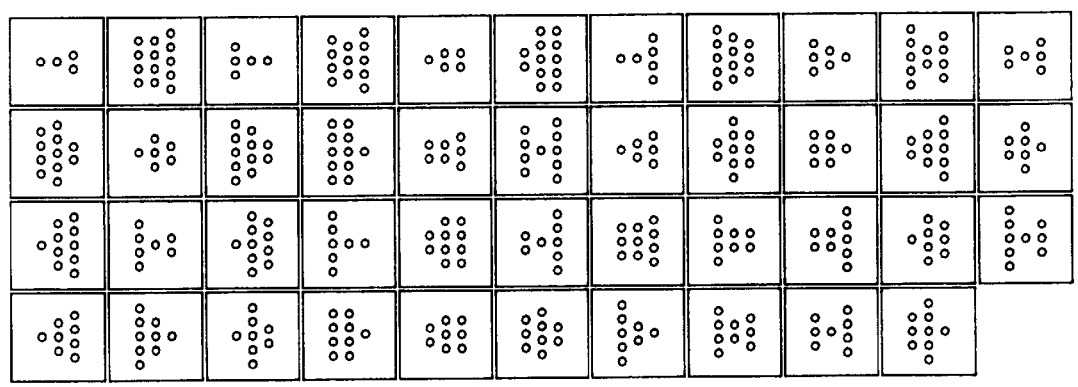
Figure 7:
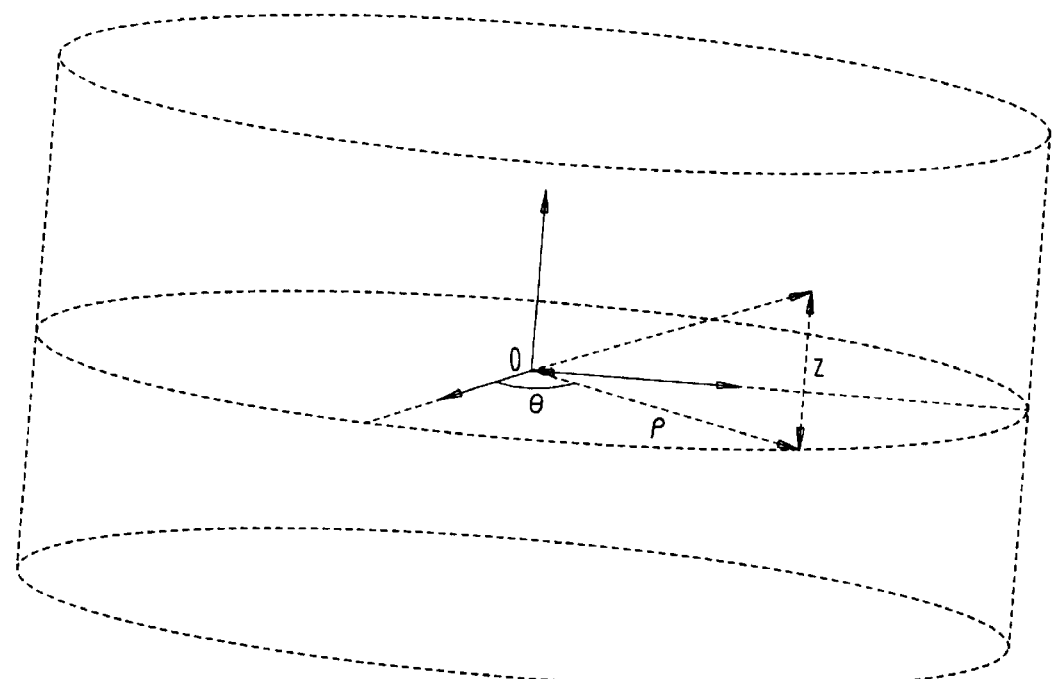
Figure 8:
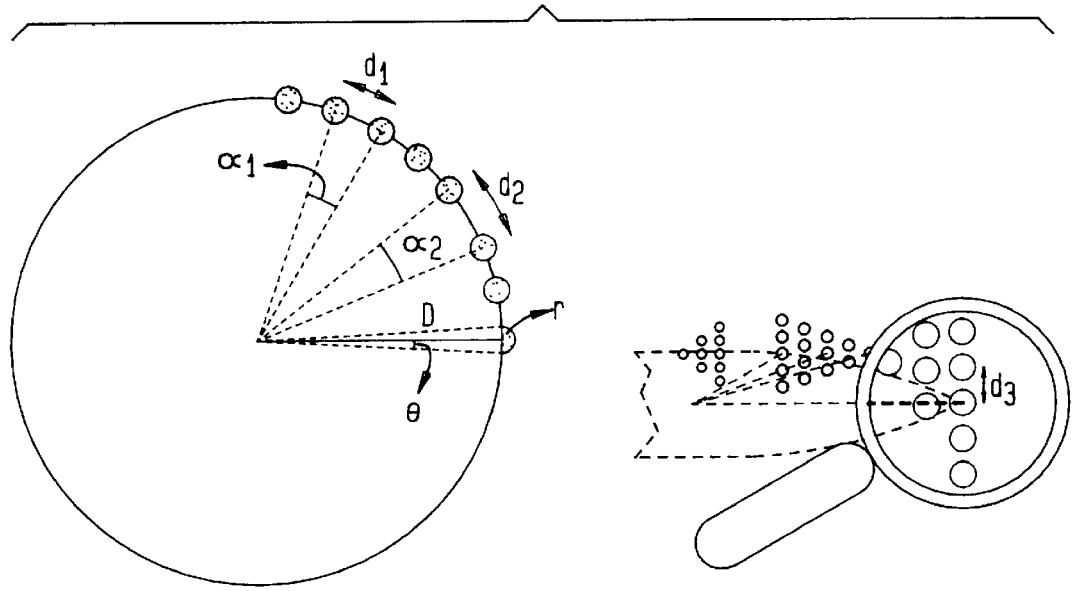
Figure 9A:
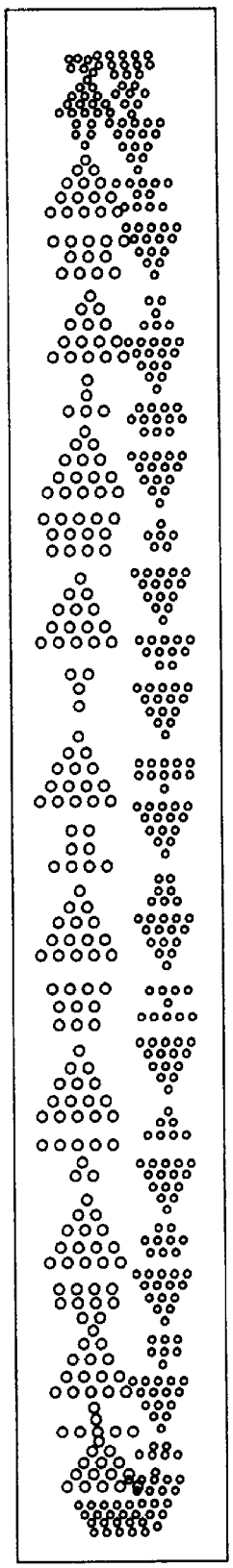
Figure 9B:
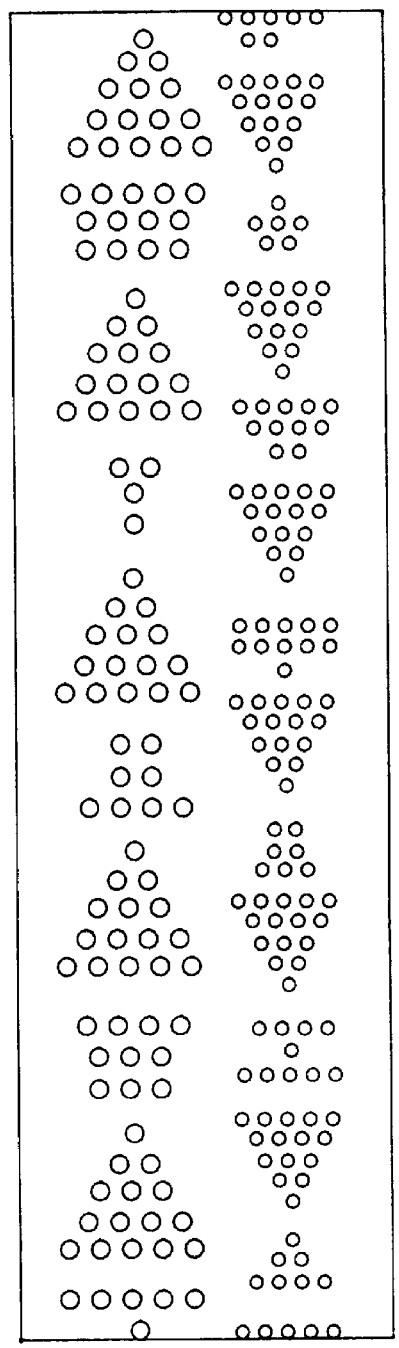

FIG. 5, applicable to an embodiment of the present invention, shows how a Blank Space is the five digit code 54321 or 12345 depending on the sign of the surface normal component in the viewing direction (a), and how this arrangement is excluded to disambiguate detection of Blank Space (b);

FIG. 6 shows a table of consecutive words for an embodiment of the present invention which table is sorted such that the total number of BB's in consecutive words varies as little as possible;

FIG. 7 shows a cylindrical coordinate system as applied to an embodiment of the present invention, wherein the center of the coordinate system is at the center of the cylindrical support and each point is defined by its three coordinates $\Theta$, $\rho$, and z;

FIG. 8 shows parameters of a calibration ring in accordance with an embodiment of the present invention, in a top view (a) and in a side view (b); and FIG. 9 shows simulation results for an X-ray image of a calibration ring in a typical X-ray imaging system in accordance with the present invention, in a complete view (a) and in a partial view (b) which is the more typical image in a local reconstruction application for the present invention.

Figure 1:
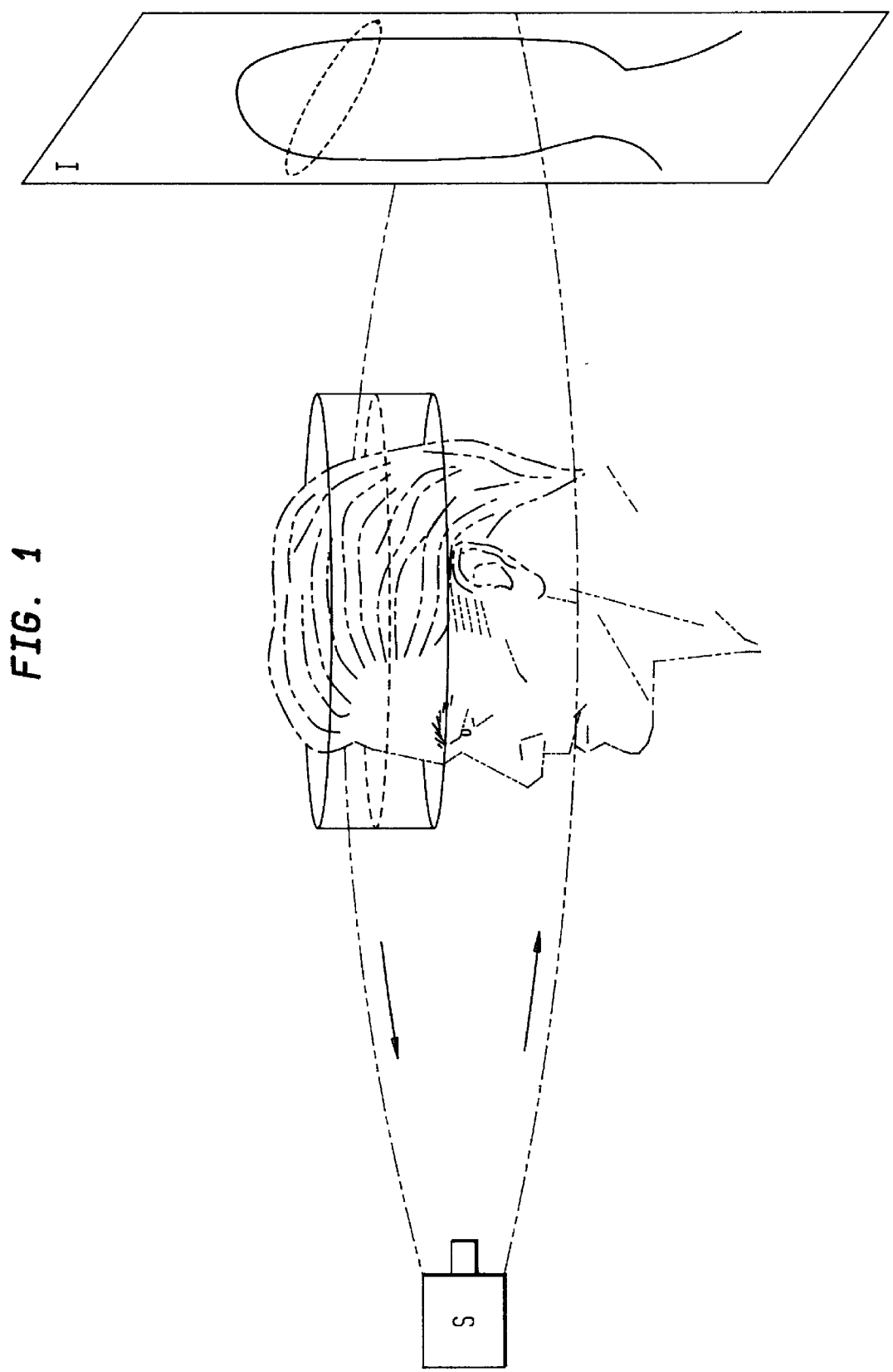
FIG. 1 shows a configuration for use in conjunction with the present invention showing the relative position of an X-ray source S, and image intensifier I, and a calibration frame F, in reference to a patient's head.
Figure 2A:
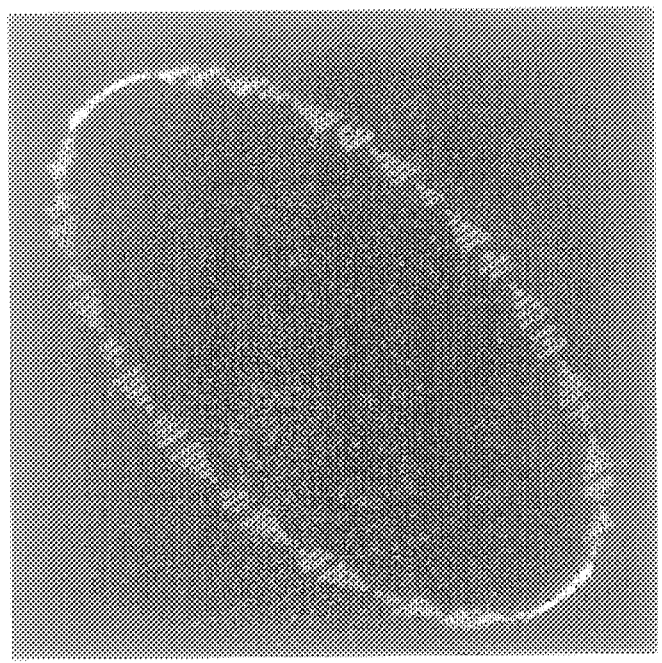
FIG. 2 shows a calibration ring in accordance with the present invention with perspective views (a) and (d), a top view (b), and a typical view in the application of the present invention (c)
Figure 2B:
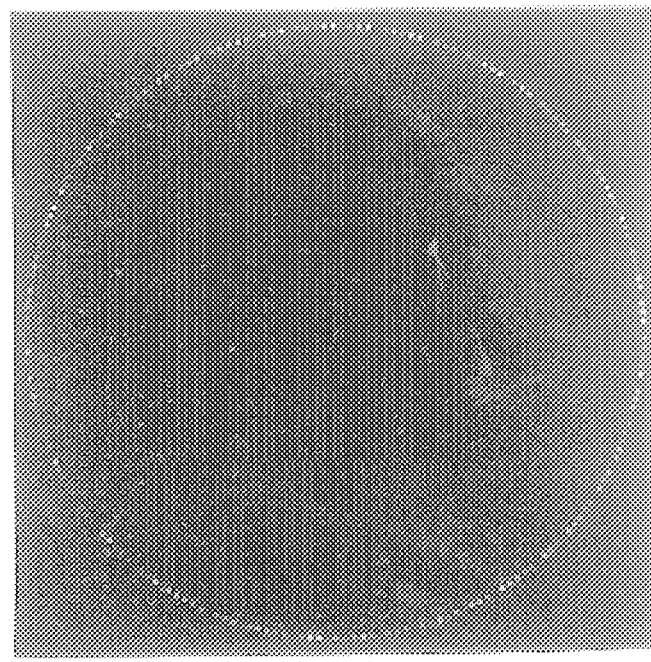
Figure 2C:
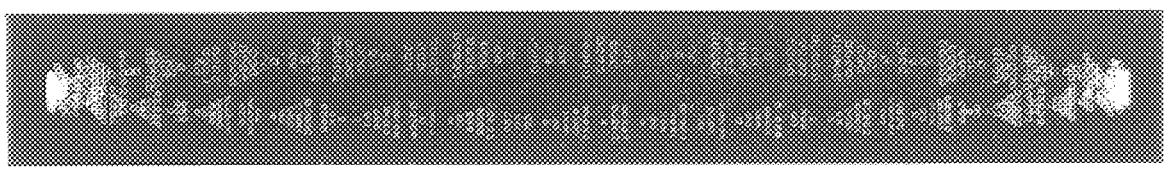
Figure 2D:
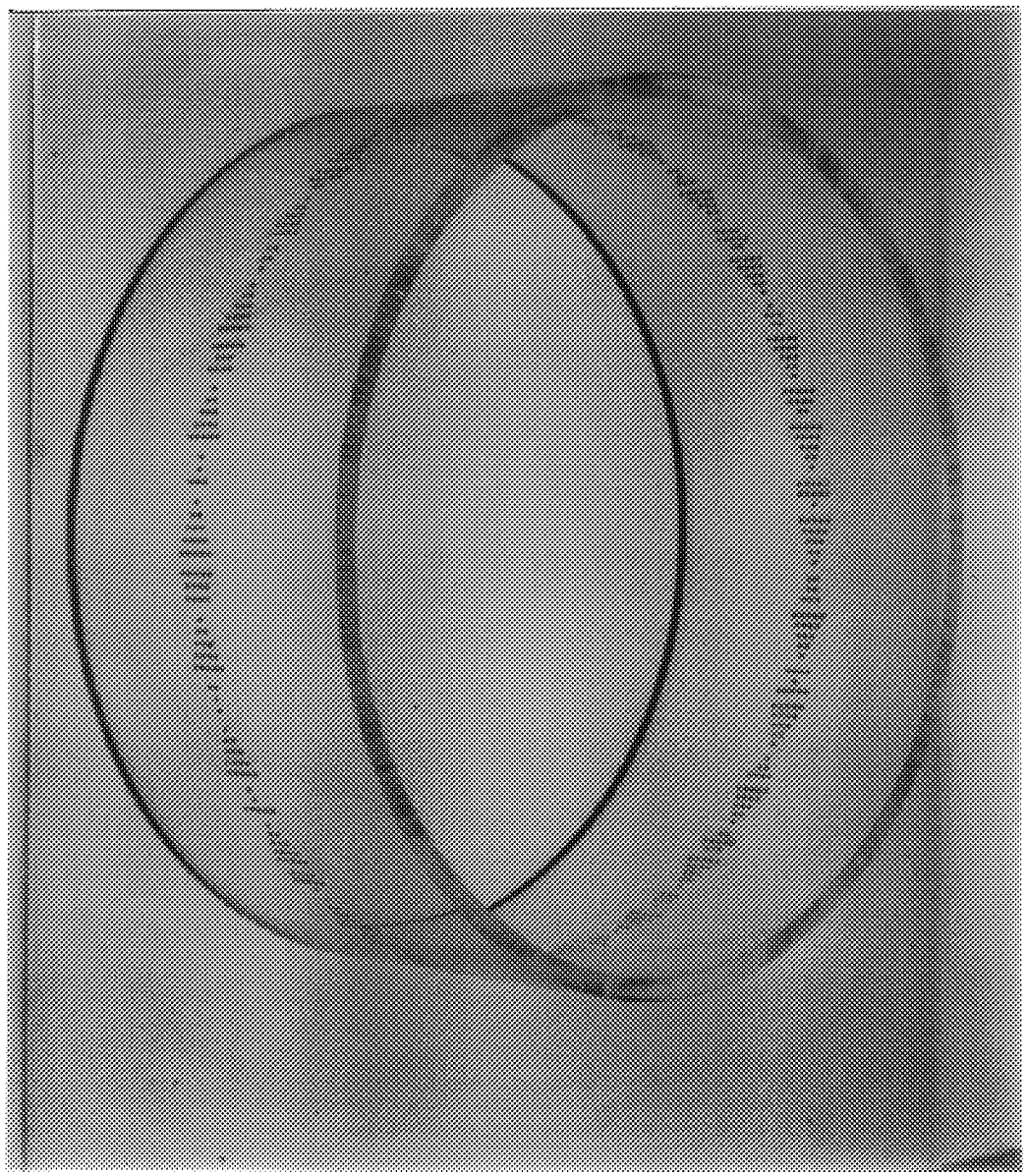
Figure 3:
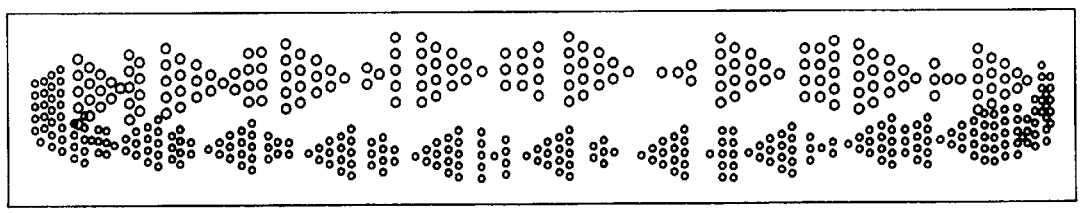
FIG. 3 shows a change in the size of spherules or ball bearings (BB's) and the spacing between them under a perspective projection, as applicable to an embodiment of the present invention.

The calibration system and apparatus in accordance with the invention are described in terms of an illustrative embodiment comprising a set of landmarks positioned around a patients head, the "calibration frame". FIG. 1 shows the relative position of an X-ray source S, an image intensifier I, the calibration frame F and a patient's head. A reference coordinate frame xyz is attached to the calibration frame. The three dimensional shape of the calibration frame is precisely known in this coordinate frame. The ball bearings incorporated in the calibration frame are made of steel which has a much higher absorption coefficient than human bones and tissue. This makes the detection and/or segmentation in the image much easier. It is noted that the procedures of detection, segmentation and calibration are known in the art and need not be further detailed herein.

A problem then is to first find the 3D-2D correspondence between the 3D model of the calibration frame and its image, and then to recover the position and orientation of the X-ray source in the reference coordinate frame xyz.

This problem is similar to what is called "recovery of absolute orientation" in photogrammetry, or "pose determination" in computer vision. It is an object of the invention that the 3D-2D correspondences can be easily and unambiguously determined. The calibration ring is utilized for the reconstruction of a small region of interest (local reconstruction). The image acquisition setup is such that the region of interest will fill the entire field of view, meaning that only a portion of the calibration ring will be present in the X-ray image. It is herein recognized that the design of the calibration ring must be smart enough so one can unambiguously determine the part of the ring that appears in the image.

The calibration frame in accordance with the present invention comprises a circular ring $R_0$ formed by a set of ball bearings (BBs). The calibration ring will be described in further detail subsequently. FIG. 2 shows a top view and perspective views of the calibration frame in accordance with the invention. It will explained further below why this is a smart disposition of calibration BBs. The calibration procedure comprises the following steps: detecting the projections of spheres (BBs) on the X-ray images based on the variation of X-ray image intensity; find the 2D-3D correspondences between image and the calibration ring; compute the orientation of the camera R and its location T in the coordinate system associated with the calibration ring.

The design of the calibration ring is important with regard to the invention since it affects all three steps of the method. Accordingly, a design is next introduced. The present inventors have performed simulation of the structure of the calibration ring in order to illustrate performance. Different views of the calibration ring and in particular its image within a typical X-ray imaging system are shown by way of simulation procedures using the software Maple.

It is herein recognized that the calibration ring should be designed such that 3D-2D correspondence can be easily and unambiguously determined. In addition to determining such correspondence from one view only, it is desirable to find the correspondence from a partial view of the calibration frame in the event it may be necessary to focus on some particular part of, for example, a patient's brain. In accordance with the described exemplary embodiment, the calibration frame comprises a circular ring $R\_o$ formed by a set of ball bearings (BBs). Subsets of BBs are arranged vertically around the circumference of the ring $R\_o$. Sequences of such arrangements define code words in order to encode different sections of the ring. In designing this coding, the following considerations apply. The relative spacing between BBs will vary under perspective projection. Therefore, the spacing between BBs is not utilized for encoding the calibration frame.

However, the spacing for facilitating this decoding process can be utilized, as will be explained further in due course. The sizes of BBs will vary under perspective projection. Accordingly, the different sizes of BBs are not utilized for encoding the calibration frame. Thus, one may choose two BBs, one quite small and the other relatively large to make sure that, under typical perspective transformation they remain distinguishable. In this case the detection of small BBs may become quite difficult and imprecise because of their reduced size. To solve this problem, a material of high X-ray absorption coefficient may be utilized; however, this may lead in turn to image saturation for large BBs, which makes the detection of their centroid difficult and imprecise. Therefore, the same size BBs are utilized in the construction of the ring.

In accordance with an embodiment of the invention, a particular arrangement of BBs is used to define a spacing word (Blank Space) between two consecutive codes. To define the Blank Space and other code words on the Ring, the following rules are followed. No word other than Blank Space occurs more than once. In X-ray imaging, surface patches will image differently depending upon the sign of the surface normal component in the viewing direction. Therefore, a word may be projected in two different ways, one being a flipped version of the other, depending on the relative positioning of the ring and imaging system.

Figure 4:
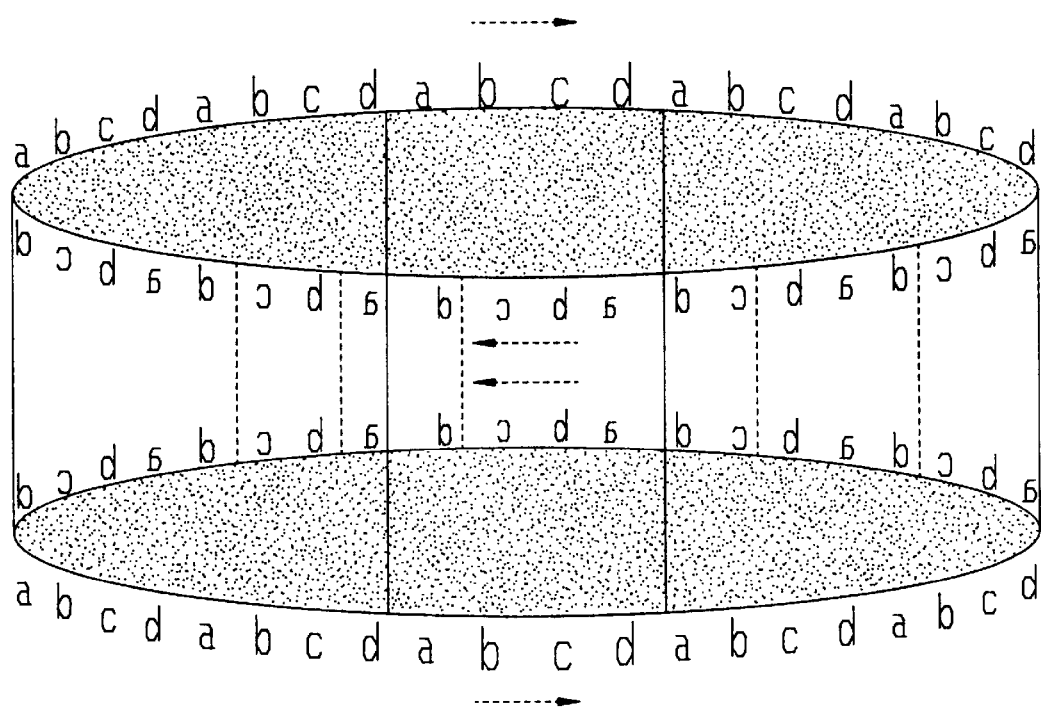
FIG. 4 shows a view of a cylinder, applicable to the present invention, wherein the center of projection is out of the cylinder between its two bases, indicating that words incorporated therein are flipped when the sign of the surface normal component in the viewing direction changes.

FIG. 4 gives a clear example of this effect. A transparent cylinder is viewed. The center of projection is out of the cylinder between its two bases. It can be noted how the words are flipped when the sign of the surface normal component in the viewing direction changes. A further rule is that a word cannot be a code word if its flipped version is a codeword. In particular, no symmetric word can be a code word. In the exemplary embodiment, the Blank Space is the five-digit code 54321 or 12345 depending on the sign of the surface normal component in the viewing direction (see FIG. 5 and FIG. 6). The positioning codes are 3 digit words in base 6. The word 234 (or 432) is excluded to disambiguate detection of Blank Space (see Fig. ) W is the set of all possible code words when following all the rules and remarks described earlier:

W=[112, 445, 311, 435, 122, 255, 114, 543, 321, 524, 213, 452, 132, 542, 551, 223, 415, 124, 253, 331, 235, 241, 145, 412, 154, 511, 244, 215, 334, 422, 225, 143, 513, 134, 531, 152, 441, 233, 342, 521, 423, 314, 351]

FIG. 6 shows a picture of W: The total number of visible BBs in partial views (see FIG. 9) of the ring should vary as little as possible. This helps keeping a uniform precision in the calibration result. The code words in W are sorted such that the total number of BBs in consecutive words varies as little as possible. This means that a code with a small number of BBs, e.g. the code 112, with only 4 BBs, is followed by a code with a large number of BBs, e.g. 112 is followed by 445. Accordingly it is preferable to use an even number of code words. Therefore, in the exemplary embodiment, the distance between consecutive BBs is modified, if necessary, in order to have an even number of code words. Blank Space has 5 digits and 15 BBs (FIG. 5 while a code word has only 3 digits and an average of 8 BBs. In a small window containing one word and one Blank Space, this leads to a small ratio between variation in number of visible BBs ±5 over their average number 23.

If the Blank Space had less digits or BBs, this ratio would undesirably increase. The design of the calibration ring may go through different changes during the testing process. Therefore, the present invention incorporates flexible design, where the radius of the ring R, radius of BBs r, the spacing between codewords $d_2$, and horizontal/vertical BBs inter-distances within a code word, respectively $d_1$ and $d_3$, are all variables. In addition to the foregoing description of the geometry of an exemplary implementation of the calibration ring, there is described in the following the designing algorithm, with an example to give different measurements.

This information is contemplated to be helpful in the design of additional embodiments for new rings as may be required, by simply varying some of the parameters. The design results in a particular arrangement of BBs. Therefore, it gives a set of BBs positions in a particular coordinate system attached to the ring. A cylindrical coordinate system is preferred as an apparently natural choice. The center of the coordinate system is taken to be at the center of the cylindrical support of the calibration ring. Each point, being the position of a BB, is defined by its three coordinates $\Theta$, $\rho$, z in FIG. 7.

Since all BBs are positioned on the ring, $\rho=R$ for all points. All the parameters in the design, $\Theta$, $\alpha_1$, $\alpha_2$, $d_1$, $d_2$, and $d_3$ are functions of the size of the calibration ring and that of the BBs (R and r). In the present exemplary embodiment, BBs of radius $r=0.6$ mm are utilized, and the BBs are located on a cylinder of radius $R=114.54$ mm. The tube used is cast acrylic, with an average outside diameter of 224.7 mm. BBs are placed on a band of a Lexan sheet of 1.58 mm thickness which is then rolled to outer circumference of the tube. It is apparent from this how the parameters of the calibration ring are defined and at each step, an example is given using the values obtained for the exemplary implementation.

First, $\Theta$ is defined (FIG. 8):

$$\Theta = \arcsin\left(\frac{r}{R}\right)$$

For example, $$\Theta = \text{Arctan}\left(\frac{0.6}{112.37}\right) = 0.0053 \text{ radians}$$

$\alpha_1$ in FIG. 8 defines the angle between centers of two consecutive BBs on the ring in radians. If these BBs are in touch, this angle equals $2*\Theta$. To facilitate detection there should be provided a spacing between BBs. The bigger are the BBs, the larger the spacing should be. Accordingly, the spacing is defined to have an angular distance of $\lambda_1*\Theta$ around the ring between BBs. In a first implementation, $\lambda_1=3$.

Therefore, $\alpha_1=2\Theta+\lambda_1\Theta$;

For example, $\alpha_1=0.026$ radians.

Therefore the arclength between centers of two consecutive BBs in a code word in millimeters is $d_1=\alpha_1R$;

For example, $d_1=2.98$ mm

In the same way, the distance between two consecutive code words can be defined. It is desirable to make this distance also a function of BB's size, $\lambda_2*\Theta$ but more than the distance between consecutive BBs inside the code.

In a first implementation, $\lambda_2=5.5$. The angle and the arclength between center of the last BB of a code word to the center of the first BB of the next code (see FIG. 8), respectively in radians and millimeters, are:

$\alpha_2=2\Theta+\lambda_2\Theta$; for example, $\alpha_2=0.0397$ radians $d_2=\alpha_2 R$; for example, $d_2=4.46$ mm.

The ring comprises a series of consecutive pairs of Blank Space and code words. If Blank Space and codewords are respectively of M and N digits, M=5 and N=3 in the first implementation, then the angle occupied by each consecutive pair around the calibration ring is:

$s=(N+M-2)\alpha_1+2\alpha_2$; For example, $s=0.238$ radians.

The maximum number of (Blank+code) words that can be positioned around the ring is then:

$$k = trunc\left(\frac{2\pi}{s}\right);$$

for example, k=26

Next, $\alpha_2$ now has to be adjusted so as to ensure a regular spacing between words. Note that if k (Blank+code) are used as defined above, then there is an extra space of $2\pi-ks$ between the last code and the first space. In the present example, this spacing is $2\pi-26*0.238=6.283-6.188=0.095$ radians. This extra space around the ring is therefore equally distributed to all spaces between consecutive code words:

$$\alpha2 = \alpha2 + \left(\frac{\pi}{k} - \frac{s}{2}\right);$$

for example, $\alpha_2=0.0414$ radians and therefore $d_2$ is also modified:

$d_2=\alpha_2R$;

for example, $d_2=4.65$ mm

The last parameter to set is the vertical distance between BBs, $d_3$ in FIG. 8. If the two BBs touch each other then $d_3=2r$. This distance should also be a function of the BB's radius $d_3=2*r+\lambda_3*r$. In addition, $\lambda_3$ should be chosen such that a vertically arranged group of BBs, defining one digit of a code word, would be easily separated from the neighboring other digits. This means that a condition should be imposed that $\lambda_3<\lambda_1<\lambda_2$.

In the first implementation, $\lambda_3$ is taken as $\lambda_3=1$ and $d_3=4.2r=2.5$ mm.

Now the ring can be built up. The second cylindrical coordinates of all points on the ring are the same $\rho=R$. The two other parameters, $\Theta$ and z define the position of each BB on the ring. The procedure begins at the point of coordinates $\{\theta=0, \rho=R, z=0\}$, or simply $\{0,R,0\}$. It then places appropriately all words and blank space around the ring. It indeed alternates a Blank Space and a word W[i], i=1 .. s, from the coding table of the coding table of FIG. 6.

Unless BBs are too small or the ring is too large, W will always provide enough code words (more than s—s=26 in the first implementation). A final verification is made that an even number of code words is utilized and if not, $\lambda_1$ and $\lambda_2$ are modified and, in consequence $l_1$ and $l_2$, to have an even number of code words around the Calibration Ring.

613 BBs are used in the first design. The tables following in the Appendix give the position of all 613 BBs. A complete simulation of the calibration ring and the imaging geometry has been built, using Maple. FIG. 9 simulates the image obtainable with a typical X-ray imaging geometry. In this simulation, the distance between the X-ray source and the image intensifier is 98 cm, the ring is centered 78 cm away from X-ray source, and the image size is taken to be 17 cm$^2$.

Clearly, the present invention can be implemented in conjunction with the use of a suitably programmed digital computer, using programming techniques known in the art.

The invention has been described by way of exemplary embodiments. It will nevertheless be understood by those of skill in the art to which it pertains that various changes and modifications can be made without departing from the teaching and spirit of the invention. For example, it will be apparent that various encoding schemes are possible as variants of those herein described. Furthermore, it will be apparent that an inversion whereby opaque and transparent portions are interchanged is feasible without any significant alteration of the operation. Such changes and the like are intended to be within the scope of the invention, which is defined by the claims following.

What is claimed is:

1. System for X-ray geometry calibration, comprising:
    a calibration frame adapted for mounting proximate to at least a portion of a patient's body;
    an X-ray source;

a target at a given orientation and distance from said portion of a patient's body for cooperating with said X-ray source for forming an image of said portion of a patient's body and a two-dimensional image of at least an associated portion of said calibration frame; and wherein said calibration frame includes encoding means for uniquely determining correspondence between said image of said associated portion of said calibration frame and said calibration frame such that said orientation and distance can be determined uniquely from said image of said associated portion of said calibration frame, even when said image of said associated portion represents less than the whole of said calibration frame.

2. System for X-ray geometry calibration in accordance with claim 1, wherein said image of said portion of a patient's body and of said associated portion of said calibration frame is contained in a two-dimensional surface.

3. System for X-ray geometry calibration in accordance with claim 1, wherein said calibration frame is adapted for fastening to a patient's head.

4. System for X-ray geometry calibration in accordance with claim 1, wherein said calibration frame exhibits a three-dimensional form.

5. System for X-ray geometry calibration in accordance with claim 1, wherein said image of said portion of a patient's body and of said associated portion of said calibration frame is in the form of a ring.

6. System for X-ray geometry calibration in accordance with claim 1, wherein said calibration frame is adapted for being fastened to said portion of a patient's body.

7. System for X-ray geometry calibration in accordance with claim 1, wherein said image of said portion of a patient's body and of said associated portion of said calibration frame is contained in a substantially flat plane.

8. System for X-ray geometry calibration in accordance with claim 7, wherein said encoding means comprises at least a portion of said calibration frame exhibiting first portions thereof that are relatively opaque to X-rays and second portions that are relatively transparent to X-rays.

9. System for X-ray geometry calibration in accordance with claim 8, wherein said encoding means comprises an encoded arrangement of said first and second portions.

10. System for X-ray geometry calibration in accordance with claim 8, wherein said encoding means comprises an encoded arrangement of said first portions.

11. System for X-ray geometry calibration in accordance with claim 10, wherein said first portions of said calibration frame are formed by metallic spherules.

12. System for X-ray geometry calibration in accordance with claim 8, wherein said encoding means comprises an encoded arrangement of said second portions.

13. System for X-ray geometry calibration in accordance with claim 12, wherein said second portions of said calibration frame are formed by holes in said calibration frame.

14. System for X-ray geometry calibration in accordance with claim 1, wherein said calibration frame exhibits a three-dimensional form.

15. System for X-ray geometry calibration in accordance with claim 14, wherein said calibration frame exhibits characteristics such that it can be determined from said image in said substantially flat plane which portions of said three-dimensional form are proximate said image in said substantially flat plane and which portions are distal therefrom.

16. System for X-ray geometry calibration in accordance with claim 15, wherein said calibration frame exhibits a three-dimensional form.

17. System for X-ray geometry calibration in accordance with claim 1, wherein said calibration frame comprises a flat ribbon-like structure.

18. System for X-ray geometry calibration in accordance with claim 17, wherein said flat ribbon-like structure is formed into an endless loop.

19. System for X-ray geometry calibration in accordance with claim 1, wherein said calibration frame comprises a substrate portion of a material that is relatively opaque to X-rays and a plurality of points in said substrate portion which are relatively transparent to X-rays.

20. System for X-ray geometry calibration in accordance with claim 19, wherein said points in said substrate portion comprise holes.

21. System for X-ray geometry calibration in accordance with claim 1, wherein said image of said portion of a patient's body and of said associated portion of said calibration frame is contained in a substantially flat plane.

22. System for X-ray geometry calibration in accordance with claim 21, wherein said codes arrangement results in a pattern in said image such that the position and orientation of said calibration frame can be uniquely determined from said image in a substantially flat plane.

23. System for X-ray geometry calibration in accordance with claim 1, wherein said calibration frame comprises a flat ribbon-like structure.

24. System for X-ray geometry calibration in accordance with claim 23, wherein said flat ribbon-like structure is formed into an endless loop.

25. System for X-ray geometry calibration, comprising:
a calibration frame associated with a portion of a patient's body;
an X-ray source;
means for forming an X-ray image of said portion of a patient's body and a two-dimensional image of at least a portion of said calibration frame; and
wherein said calibration frame comprises encoding means for determining a correspondence between said image of said associated portion of said calibration frame and said calibration frame for uniquely determining said correspondence uniquely from said image of said associated portion of said calibration frames even when said two-dimensional image of said portion represents less than the whole of said calibration frame.

26. System for X-ray geometry calibration in accordance with claim 25, wherein said calibration frame includes opaque portions thereof that are relatively opaque to X-rays and transparent portions that are relatively transparent to X-rays.

27. System for X-ray geometry calibration in accordance with claim 26, wherein said opaque portions form a coded arrangement.

28. System for X-ray geometry calibration in accordance with claim 26, wherein said transparent portions form a coded arrangement.

29. System for X-ray geometry calibration in accordance with claim 26, wherein said opaque and transparent portions form a coded arrangement.

30. System for X-ray geometry calibration in accordance with claim 26, wherein said calibration frame comprises a substrate portion of a material that is relatively transparent to X-rays and a plurality of objects imbedded in said substrate portion and being relatively opaque to X-rays.

31. System for X-ray geometry calibration in accordance with claim 30, wherein said objects imbedded in said substrate portion comprise metallic spherules.

32. A method for determining correspondence between an X-ray image of a calibration frame associated with at least a portion of the body of a patient and the position of said calibration frame with respect to X-ray apparatus, comprising the steps of:

(a) positioning an encoded three-dimensional calibration frame relative to at least a portion of a patient's body;

(b) exposing said portion of a patient's body and at least a portion of said calibration frame to an X-ray source at a given orientation and distance therefrom so as to form a projected image of said portion of a patient's body a two-dimensional image of at least a portion of said portion of said calibration frame; and (c) uniquely determining a correspondence between said image of said portion of said calibration frame and said three-dimensional calibration frame from observations of said image such that said orientation and distance are uniquely determined from said image of said associated portion of said calibration frame, even when said image of said associated portion represents less than the whole of said calibration frame.

33. A method for determining correspondence between an X-ray image of a calibration frame associated with at least a portion of the body of a patient and the position of said calibration frame with respect to X-ray apparatus, comprising the steps of:

(a) positioning an encoded three-dimensional calibration frame relative to at least a portion of a patient's body, said calibration frame including therein an arrangement of spherules;

(b) exposing said portion of a patient's body and at least a portion of said calibration frame to an X-ray source at a given orientation and distance therefrom so as to form a projected image of said portion of a patient's body and of said portion of said calibration frame; and (c) uniquely determining a correspondence between said image of said portion of said calibration frame and said three-dimensional calibration frame from observations of said image; and (d) computing said orientation and distance.

* * * * *